United States Patent [19]

Elaissari et al.

[11] Patent Number: 6,133,047
[45] Date of Patent: Oct. 17, 2000

[54] SUPERPARAMAGNETIC MONODISPERSE PARTICLES

[75] Inventors: Abdelhamid Elaissari, Lyons; Christian Pichot, Corbas; Bernard Mandrand, Villeurbanne; Florence Sauzedde, Lyons, all of France

[73] Assignee: Bio Merieux, Marcy l'Etoile, France

[21] Appl. No.: 08/983,040

[22] PCT Filed: May 23, 1997

[86] PCT No.: PCT/FR97/00912

§ 371 Date: Jan. 15, 1998

§ 102(e) Date: Jan. 15, 1998

[87] PCT Pub. No.: WO97/45202

PCT Pub. Date: Dec. 4, 1997

[30] Foreign Application Priority Data

May 24, 1996 [FR] France .................................. 96 06765

[51] Int. Cl.[7] ...................... G01N 33/553; G01N 33/566; B32B 5/16; B05D 5/12

[52] U.S. Cl. .......................... 436/526; 436/501; 436/535; 436/531; 436/173; 436/806; 436/824; 428/402; 428/402.24; 428/403; 428/407; 427/2.13; 427/128; 427/127; 427/215; 427/131; 427/132; 427/214; 427/216; 427/217; 427/221; 427/222; 427/404; 427/338; 427/405; 427/407.1; 427/409

[58] Field of Search ................................ 427/2.13, 128, 427/131, 132, 127, 213, 214, 216, 217, 221, 222, 404, 338, 405, 407.1, 409, 414, 419.2; 436/526, 535, 501, 824, 531, 173, 806; 252/62.51, 62.53, 62.54, 62.56, 62.52; 428/402, 402.24, 403, 407

[56] References Cited

U.S. PATENT DOCUMENTS

| | | |
|---|---|---|
| 4,157,323 | 6/1979 | Yen et al. ................................ 260/29.7 |
| 4,177,253 | 12/1979 | Davies et al. ................................ 424/1 |
| 4,206,094 | 6/1980 | Yen et al. .................................... 260/8 |
| 4,329,241 | 5/1982 | Massart . |
| 4,490,436 | 12/1984 | Kawakami et al. ..................... 428/403 |
| 4,628,037 | 12/1986 | Chagnon et al. ........................ 426/526 |
| 4,871,716 | 10/1989 | Longo et al. ................................ 514/2 |
| 4,971,162 | 11/1990 | Vanderhoff et al. ..................... 524/458 |
| 4,981,625 | 1/1991 | Rhim et al. ................................ 264/13 |
| 4,985,233 | 1/1991 | Klaveness et al. .......................... 424/9 |
| 4,988,568 | 1/1991 | Hasegawa et al. ...................... 428/402 |
| 4,996,265 | 2/1991 | Okubo et al. ............................ 525/242 |
| 5,043,407 | 8/1991 | Hasegawa et al. ................... 526/307.6 |
| 5,076,950 | 12/1991 | Ullman et al. ........................ 252/62.51 |
| 5,091,206 | 2/1992 | Wang et al. ................................ 427/2 |
| 5,106,903 | 4/1992 | Vanderhoff et al. .................... 524/458 |
| 5,110,624 | 5/1992 | Noble et al. ............................. 427/212 |
| 5,328,681 | 7/1994 | Kito et al. .................................... 424/9 |
| 5,411,730 | 5/1995 | Kirpotin et al. ........................ 424/322 |
| 5,648,124 | 7/1997 | Sutor ....................................... 427/475 |

FOREIGN PATENT DOCUMENTS

| | | |
|---|---|---|
| 0 106 873 | 5/1984 | European Pat. Off. . |
| 0 446 260 | 9/1991 | European Pat. Off. . |
| 0 585 868 | 3/1994 | European Pat. Off. . |
| WO 91/09141 | 6/1991 | WIPO . |

OTHER PUBLICATIONS

A. Kondo et al., "Development and Application of Thermo–Sensitive Magnetic Immunomicrospheres For Antibody Purification", *Appl. Microbiol. Biotechnol*, vol. 41, pp. 99–105, (1994).

*Primary Examiner*—Christopher L. Chin
*Assistant Examiner*—Pensee T. Do
*Attorney, Agent, or Firm*—Oliff & Berridge, PLC

[57] ABSTRACT

The superparamagnetic monodispersed particles comprise a core of a first polymer, an internal layer of a second polymer coating the core and in which a magnetic material is distributed, and an external layer of a third polymer coating the magnetic layer and capable of interacting with at least one biological molecule. At least the second polymer is heat sensitive and has a predetermined lower critical solubility temperature (LCST) of 15–65° C. These particles may be used to isolate at least one biological molecule from a liquid specimen.

23 Claims, No Drawings

SUPERPARAMAGNETIC MONODISPERSE PARTICLES

The present invention relates to monodisperse superparamagnetic particles, to their process of production and to their uses, in particular in biology for the isolation of biological molecules.

Monodisperse superparamagnetic particles are disclosed in the prior art. By way of illustration, documents EP-0,106,873 and EP-0,446,260 describe monodisperse superparamagnetic particles comprising a porous core based on a polystyrene/divinylbenzene copolymer in which particles of magnetic iron oxide are incorporated, and a functionalized external layer capable of interacting with nucleic acid probes.

According to the process for producing the particles described in these documents, the magnetic iron oxides are incorporated by precipitation of the corresponding salts. This limits the content of magnetic filler incorporated and makes it possible to obtain the magnetic filler only as a monolayer.

Document EP-0,585,868 describes magnetic particles consisting of a core based on a first polymer and on a magnetic layer covering the core, which layer consists of a second polymer, in which the ferrite-based magnetic material is distributed, and is capable of interacting with an antigen or an antibody, the magnetic material being deposited by precipitation of iron salts.

The magnetic material incorporated is directly exposed to the subsequent treatments of the particles and as a result there is a loss of filler during use of the particles. This may lead to problems, in particular to problems of enzyme inhibition and of denaturation of biological entities.

According to the invention, particles which are superparamagnetic and which have a magnetic filler distributed very homogeneously are used, the content of which may vary between 1 and 80%, in particular from 25 to 80% by weight with respect to the polymer(s) constituting the particles. The present invention makes it possible to achieve high contents of incorporated magnetic filler, in particular since the process employed makes it possible to distribute the magnetic filler in the form of multilayers. This results in a considerable advantage, namely the possibility of effective separation of the particles of the invention from the specimen, without having recourse to the combined action of another separation technique, such as flocculation.

The magnetic filler is in the form of nano-particles which are incorporated in the particles in a substantially irreversible manner, i.e. without loss by release, whatever the subsequent treatments which are applied to them, in particular in the specimen, namely rinsing operations, variations in temperature, in pH, etc.

The properties of the particles of the invention result from their particular structure and particular composition and more specifically from the presence of a constituent heat-sensitive polymer at least for supporting the magnetic material.

A process for obtaining magnetic particles, comprising a core based on a first polymer consisting of a polystyrene and in which a magnetic material is distributed, and a hydrophilic layer covering the core, based on a heat-sensitive polymer consisting of poly(N-isopropylacrylamide), is known from the article by A. KONDO, (A. KONDO, H. KAMURA and K. HIGASHITANI (1994), Appl. Microbiol. Biotechnol., 41, 99–105). The process described comprises the following steps:

in a first step, for obtaining the magnetic core, the magnetic material is brought into contact with styrene in the presence of a polymerization initiator and then in a second step, for obtaining the hydrophilic layer, the core obtained is brought into contact with N-isopropylacrylamide and methacrylic acid, in the presence of the above polymerization initiator.

Bovine serum albumin is fixed to the particles thus obtained in order subsequently to isolate antibodies directed against the bovine albumin serum present in a specimen.

The drawback of these particles occurs in the step for separating them: these particles incorporate a small amount of magnetic filler and furthermore have sizes which vary greatly, considerably limiting the effectiveness of an applied magnetic field for separating the particles. Thus, in order to ensure as efficient as possible a separation of these particles in the specimen, the authors have employed thermoflocculation in which the temperature of the specimen is increased, this having the effect of completing the action of a magnetic field.

The requirement of an additional separation technique results from the particles obtained which have the following drawbacks:

low contents of incorporated magnetic filler, non-homogeneous distribution of the magnetic filler and formation of non-monodisperse particles.

The particles of the invention are intended for isolating biological molecules essentially by applying a magnetic field, independently of any variations in temperature, pH or ion strength.

The monodisperse superparamagnetic particles of the invention have a predetermined size of between 0.1 and 10 $\mu$m and comprise:

a core based on a first polymer, an internal layer, called the magnetic layer, covering the core, based on a second polymer, in which layer a magnetic material is distributed, and an external layer, called the encapsulation layer, optionally functionalized, covering the magnetic layer, based on a third polymer and capable of interacting with at least one biological molecule, at least the second polymer being heat-sensitive and having a predetermined lower critical solubility temperature (LCST) of between 15 and 65° C. and preferably between 25 and 50° C.

Advantageously, the second polymer is obtained by polymerization of (1) a water-soluble monomer of acrylamide or of an acrylamide derivative, such as N-isopropylacrylamide (NIPAM), (2) at least one crosslinking agent, such as N,N-methylenebisacrylamide and (3) at least one functional, cationic and water-soluble monomer different from the monomer (1), such as 2-aminoethyl-methacrylate chloride. A second preferred polymer is PNIPAM [poly(N-isopropylacrylamide)].

The first polymer may be identical to the second polymer or different from the second polymer and, in the latter case, the first polymer will preferably be a polymer having a hydrophobic character and in particular a polystyrene or a polymethyl methacrylate.

The third polymer is a polymer compatible with the second polymer and is selected from hydrophilic polymers, in particular acrylamide derivatives and preferably PNIPAM. When this third polymer is functionalized, it bears one or more functional groups selected from carboxylic, aldehyde, thiol and amine functional groups.

A second subject of the invention is a process for obtaining particles as defined above, which comprises the following steps:

in a step (a), called the step for obtaining the first polymer, the first polymer is obtained by polymerization of the suitable monomer or monomers, in a step (b), called the step for obtaining the second polymer, a sol of the second polymer is obtained by polymerization in aqueous phase of (1) a water-soluble monomer of acrylamide or of an acrylamide derivative, (2) at least one crosslinking agent and (3) at least one functional, cationic and water-soluble monomer different from the monomer (1), in a step (c), called the step for adsorption of the magnetic material, the magnetic material is brought into contact with the first and second polymers at a temperature below the LCST of the second polymer, in a step (d), called the step for obtaining the magnetic layer, the reaction mixture obtained in (c) is raised to a temperature above the LCST of the second polymer, and in a step (e), called the encapsulation step, the mixture obtained in (d) is brought into contact, in aqueous phase, with the monomer or monomers suitable for obtaining the third polymer by polymerization.

Steps (a) and (b) are, according to a variant of the process, carried out simultaneously, in particular but not restrictively when the first polymer is identical to the second polymer.

For step (b) and optionally step (a), the polymerization reactants are preferably selected as follows:

the monomer (1) is preferably selected from N-alkylacrylamides and N,N-dialkylacrylamides, in particular from N-isopropylacrylamide, N-ethylmethacrylamide, N-n-propylacrylamide, N-n-propylmethacrylamide, N-isopropylmethacrylamide, N-cyclopropylacrylamide, N,N-diethylacrylamide, N-methyl-N-isopropylacrylamide, N-methyl-N-n-propylacrylamide, the monomer (1) preferably being N-isopropylacrylamide (NIPAM), the functional monomer or monomers (3) are selected from acrylic and methacrylic derivatives, 2-aminoethyl methacrylate (AEM) chloride, N-vinylpyridine derivatives, trialkylammonium derivatives and isothiouronium chloride derivatives and optionally, the crosslinking agent (2) is water-soluble and is selected from N,N-methylenebisacrylamide (MBA) and ethylene glycol dimethacrylate.

For step (c), the adsorption of the magnetic material on the second polymer results from electrostatic interactions between particles of opposite charges. The reaction medium for the adsorption is an aqueous phase, the ion-strength and pH parameters of which are controlled.

The invention furthermore relates to applications of the particles defined hereinabove. Thus, the particles can be used in particular to capture and then separate, in a liquid specimen, at least one biological molecule, in particular selected from proteins, antibodies, fragments of antibodies, antigens, polypeptides, enzymes, haptens, nucleic acids and fragments of nucleic acids. The biological molecule or molecules are fixed to the particles, directly or indirectly, by adsorption or by covalent bonding, and, in the latter case, via a ligand for example.

Examples of particular uses of the particles of the invention are as follows:

use as a tracer after magnetic concentration on a solid phase:

in this case, the particle is counted after scanning the surface using an atomic force microscope tip or after direct microscopic observation, or using a camera; the magnetic particles may be detected because of their metallic charge and may be measured using a magnet-ometer or any other system of the type for reading a credit card; in order to make it easier to concentrate the particles on the surface, a permanent magnet or an electromagnet may be placed below or above the surface used for the detection; magnetic concentration will preferably take place if a limited number of particles is used, for example the quantity sufficient to cover from one to ten times the surface area if the process is static and optionally a greater quantity if the concentration is dynamic, by controlled circulation of liquid on the reactive surface;

uses of the particles coupled to an appropriate biological ligand within an agglutination reaction protocol; the size of the particles may be monitored directly in the medium or after magnetic attraction;

use of the particles for carrying reactants into a device of the capillary type, a set of electromagnets allowing the particles to be moved;

use of the particles for creating preferred channels and/or for obstructing liquid distribution channels;

use of the particles for transporting therapeutic substances right to their targets:

the active principle is adsorbed or transiently coupled by covalency to the surface of the particle and a suitable magnetic field is applied in order to move the combination of particle and therapeutic substance.

Another subject of the invention is a process for isolating, in a liquid specimen, at least one biological molecule, in which:

particles according to the invention are used, said specimen is brought into contact with said particles, by incubation, a magnetic field is applied to the mixture obtained and the particles are separated from the specimen.

Of course, the separation of the particles, which forms the subject of this latter process, is different from the separation of the biological molecules which is included in the notion of isolation. In the former case, it is a question of separating, from the liquid specimen, those particles to which the biological molecule or molecules are fixed, by the action of a magnetic field.

Lastly, a final subject of the invention is a reactive means for isolating biological molecules comprising a dispersion, in aqueous medium, of particles as defined above.

Before describing the present invention in greater detail, certain terms employed in the description will be defined.

The expression superparamagnetic particles is understood to mean particles containing particles of a magnetic material, guaranteeing, after removal of the magnetic field, the absence of any remanent magnetization.

The expression monodisperse particles is understood to mean particles having approximately the same size, and more specifically a size which varies by at most 5% with respect to a given and chosen average size.

The expression "to isolate a biological molecule", according to the invention, comprises the separation and detection of a biological molecule, the enrichment of a fraction within a biological molecule, using a specific or non-specific method of isolation, qualitatively and/or quantitatively, directly or indirectly, for example via a ligand fixed to the particles.

EXAMPLE 1

Production of the First and Second Polymers

1) The first and second polymers are different, the first being a polystyrene and the second being PNIPAM The production processes detailed below are used [lacuna] radical polymerization in heterogeneous medium, using the following initial reactants:

for the first polymer:
  the monomer is styrene (St) (Janssen),
for the second polymer:
  the monomer (1) is N-isopropylacrylamide (NIPAM) (Kodak),
  the crosslinking agent is N,N-methylenebisacrylamide (MBA) (Aldrich),
  the functional monomer (3) is 2-aminoethyl methacrylate (AEM) chloride (Kodak),
  the polymerization initiator is 2,2'-azobis (amidinopropane) chloride (V50) (Wako), and NaCl was used to adjust the ion strength.

1.1) Closed-reactor (Batch) Polymerization

All the aforementioned monomers are introduced into the reactor before the start of the polymerization reaction together with the other reactants and without subsequent addition. This method proves to be very effective for copolymerizing a mixture of hydrophobic and hyprophilic monomers since the hydrophobic monomer (St) mainly forms the core and the hydrophilic monomer (NIPAM) forms the layer covering the core, if the polymerization takes place in aqueous phase.

The synthesis is carried out in a 250 ml reactor with constant stirring at 200 revolutions/minute and in an inert atmosphere of nitrogen. The water used, boiled and degassed under nitrogen for two hours, is introduced into the reactor, which is thermostatted at 70° C., and left under a gentle stream of nitrogen for 15 minutes so as to remove any traces of oxygen. The monomers (St, NIPAM) are introduced and degassed for a further 15 minutes before adding the initiator V50.

Formulation of the reaction mixture:

| Reactants | Mass |
|---|---|
| water | 200 ml |
| St | 18 g |
| NIPAM | 2.06 g |
| V50 | 0.2053 g |

Characteristics of the colloidal dispersion obtained:

| | |
|---|---|
| (a) diameter at 20° C. | 376 nm |
| (b) diameter at 50° C. | 330 nm |
| (c) diameter using TEM | 326 nm |
| (d) density of the dispersed phase | 10 mmol/g |

(a) diameter measured by dynamic light scattering at 20° C.
(b) diameter measured by dynamic light scattering at 50° C.
(c) diameter measured using transmission electron microscopy
(d) density of the dispersed phase expressed in mmol (amine)/g of polymer.

1.2 Polymerization on a Seed

This method consists in introducing the monomer or monomers (1) and/or (3) into a reactor containing the colloidal dispersion 1.1) already formed and perfectly characterized, in the presence of the crosslinking agent MBA. The monomer or monomers (1) and/or (3) may be added to the seed, in a single step or semi-continuously.

The polymerization reaction is carried out in a 100 ml reactor, at a temperature of 70° C., with stirring at 200 revolutions/minute. The duration of the polymerization reaction is 19 hours.

Formulation of the reaction mixture identified by the reference (PS131/132):

| Reactants | Mass (g) |
|---|---|
| Polymer according to 1.1 | 1.26 |
| NIPAM | 0.77 |
| MBA | 0.06 |
| AEM | 0.06 |
| V50 | 0.018 |

Characteristics of the sol obtained:

| | |
|---|---|
| (a) diameter at 20° C. | 610 nm |
| (b) diameter at 50° C. | 450 nm |
| (c) diameter using TEM | 305 nm |
| (d) density of the dispersed phase | 19 mmol/g |

(a) diameter measured by dynamic light scattering at 20° C.
(b) diameter measured by dynamic light scattering at 50° C.
(c) diameter measured using electron microscopy
(d) density of the dispersed phase expressed in mmol (amine)/g of polymer.

2) The First and Second Polymers are Identical and are PNIPAM

The initial reactants are those which were selected in 1) for the second polymer.

2.1) Batch Polymerization (or Closed-reactor Process)

The monomer (1) (NIPAM), the functional monomer (3) (AEM) and the crosslinking agent (MBA) are introduced together in a single step before the polymerization is initiated by adding the initiator (V50). The duration of the polymerization is 30 min.

Formulation of the polymer obtained, identified by the reference PNIPAM42:

| | |
|---|---|
| Total volume of boiled and degassed water | 250 ml |
| NIPAM | 48.51 mmol |
| MBA | 3 mmol |
| AEM | 0.48 mmol |
| V50 | 0.30 mmol |
| Temperature | 70° C. |

The characteristics of the polymer obtained after polymerization are given in the following table:

| | |
|---|---|
| diameter[a], DLS 20° C. to 20° C. [sic] | 292 nm |
| diameter[b], DLS size at 40° C. | 164 nm |
| diameter[c], TEM | 129 nm |
| concentration of AEM[d] | 14.1 μmol/g of polymer |
| LCST[e] | 31.5° C. |
| CCC[f] at 20° C. | 1.00 mol/l |

[a] diameter measured by dynamic light scattering at 20° C.
[b] diameter measured by dynamic light scattering at 40° C.
[c] diameter measured using electron microscopy
[d] density of the dispersed phase expressed in mmol (primary amine)/g of polymer.
[e] lower critical solubility temperature (LCST) determined by measuring the turbidity as a function of temperature
[f] critical coagulation concentration (CCC) at 20° C.

2.2) Semi-continuous Polymerization

The monomer (3) is introduced in two stages, at 3 min and at 6 min respectively, into the reactor which already contains the monomer (1), the crosslinking agent (2) MBA and the initiator V50, in the course of polymerization. This addition may be carried out at a constant rate of injection (polymerization by continuous addition) or else with well-controlled addition at regular intervals (semi-continuous polymerization). The aim of this polymerization method is to increase the incorporation of functional monomer(s) (3) without increasing the percentage of water-soluble polymer in the reaction mixture.

Formulation of the polymer obtained, identified by the reference PNIPAM45:

| | |
|---|---|
| Total volume of boiled and degassed water | 250 ml |
| NIPAM | 48.51 mmol |
| MBA | 3 mmol |
| AEM | 0.48 mmol |
| V50 | 0.30 mmol |
| Temperature | 70° C. |
| Additions | between 3 and 6 min. |

The characteristics of the polymer PNIPAM45 obtained after polymerization are given in the following table:

| | |
|---|---|
| diameter[a], DLS 20° C. to 20° C. [sic] | 823 nm |
| diameter[b], DLS size at 40° C. | 530 nm |
| diameter[c], TEM | 327 nm |
| concentration of AEM[d] | 10.0 µmol/g of polymer |
| LCST[e] | 32° C. |
| CCC[f] at 20° C. | 1.00 mol/l |

[a]diameter measured by dynamic light scattering at 20° C.
[b]diameter measured by dynamic light scattering at 40° C.
[c]diameter measured using electron microscopy
[d]density of the dispersed phase expressed in mmol (primary amine)/g of polymer.
[e]lower critical solubility temperature (LCST) determined by measuring the turbidity as a function of temperature
[f]critical coagulation concentration (CCC) at 20° C.

2.3) Polymerization on Seed

This method consists in introducing the monomer or monomers (1) and/or (3) into a reaction medium containing a sol of the polymer produced beforehand according to 2.1 and perfectly characterized.

Formulation of the reaction mixture:

A volume of 40 ml of seed 2.1 with a concentration of 4.5 g per 100 ml is used. The reactants were added, diluted in a volume of 5 ml of water. The molar percentages of NIPAM, MBA and V50 added in the second step are identical to those of the seed as in 2.1. On the other hand, the concentration of functional monomer (3) is controlled (increased or decreased depending on the desired density of dispersed phase); in the present case, 10% of AEM is added with respect to the monomer (1) NIPAM.

The characteristics of the polymer identified by the reference PNIPAM94), which was obtained using the operating method described in 2.1, are given in the following table:

| | |
|---|---|
| diameter[a], DLS 20° C. to 20° C. [sic] | 504 nm |
| diameter[b], DLS size at 40° C. | 290 nm |
| diameter[c], TEM | 176 nm |
| concentration of AEM[d] | 22.4 µmol/g of polymer |
| LCST[e] | 32° C. |
| CCC[f] at 20° C. | 1.10 mol/l |

[a]diameter measured by dynamic light scattering at 20° C.
[b]diameter measured by dynamic light scattering at 40° C.
[c]diameter measured using electron microscopy
[d]density of the dispersed phase expressed in mmol (primary amine)/g of polymer.
[e]lower critical solubility temperature (LCST) determined by measuring the turbidity as a function of temperature
[f]critical coagulation concentration (CCC) at 20° C.

EXAMPLE 2

Synthesis and Characterization of the Ionic Ferrofluids Intended to be Incorporated into the Layer of the Second Polymer The operating method was carried out, with the results mentioned in U.S. Pat. No. 4,329,241.

The physical properties of the ferrofluids produced according to this document are given in the following summary table:

| Properties | Values | Methods |
|---|---|---|
| diameters (nm) and dispersity | 15 ± 3 | AFM (atomic force microscopy) |
| | 7 ± 1 | TEM (transmission electron microscopy) |
| | 9.5 ± 2 | magnetization (measurement of the magnetization) |
| | 11 ± 1 | XR (X-rays) |
| thickness of the non-magnetic layer (nm) | 0.1 | magnetization |
| specific magnetization | 422 kA/m | magnetization |
| charge density (C/m$^2$) | 1.5 | conductimetry |
| pH | 7–8 | pH measurement |
| conductivity | 1 mS | conductimetry |

The method of synthesis, by the precipitation of iron oxides, makes it possible, from the results of the various methods of characterization, to obtain an anionic ferrofluid which is stable between pH 6 and pH 8, has a size of the order of ten nm and is superparamagnetic. The analyses were carried out for the various ferrofluids obtained using the same operating method: the results obtained are reproducible from one ferrofluid to another.

Since the ferrofluid particles are negatively charged, it is therefore possible for these particles to be adsorbed on a polymer of opposite charge (positively charged) via electrostatic interactions.

EXAMPLE 3

Adsorption of the Magnetic Filler on the Layer of Second Polymer

The second polymer and the magnetic filler (Example 2) have charges of opposite sign. This promotes strong adsorption, mainly via electrostatic interactions, of the magnetic filler on the polymer. The magnetic filler is placed in excess with respect to the concentration of polymer (Example 1) and the adsorption is carried out under conditions such that the degree of coverage of the surface of the second polymer is greater than 30%. 6.4 ml of the sol of the polymer obtained in Example 1 (1.2; concentration=94.5 g/l) are progressively added, in a 200 ml flask, to 29 ml of the ferrofluid obtained in Example 2 (concentration=23 g/l). After adsorption of the ferrite for 15 minutes, the excess ferrofluid is removed by placing the flask on a magnet so as to separate the polymer particles covered with ferrite. The supernatant liquid is removed, assayed and replaced by the same volume of boiled and degassed water. The flask containing the polymer covered with ferrite is again placed on the magnet so as to check that no ferrite in solution remains (clear supernatant liquid).

The table presented below gives the amount of ferrite adsorbed on the hairy latex particles of Example 1.1:

| Code | Amount adsorbed in g/g of latex | mass % adsorbed |
| --- | --- | --- |
| ENC10 | 6.63 | 45 |
| ENC11 | 6.67 | 46 |
| ENC13 | 4.70 | 40 |
| ENC12 | 5.30 | 37 |
| ENC16 | 5.00 | 40 |

EXAMPLE 4

Encapsulation of the Particles

The process of encapsulating the magnetic filler after the adsorption step consists in polymerizing, in aqueous medium, one or more monomers with a copolymerizable crosslinking agent, in the presence of a saturated suspension of magnetic polymer (Example 3). The monomers chosen may be functional and thus, in this case, be useful for the grafting or adsorption of biological molecules. This method makes it possible to obtain a magnetic polymer whose interface may be easily modified depending on the uses: a hydrophobic surface for the adsorption of a protein or a functional hydrophilic surface for chemical grafting, for example.

The encapsulation process described in this example relies on the use of an initiator and of a mixture of monomers and of a crosslinking agent. 40 ml of ferrite-covered polymer (Example 3) are introduced into a reactor thermostatted at 70° C. The monomers are then introduced into a 4 ml volume of boiled and degassed water. The polymerization time is three hours starting from the introduction of the initiator. The monomers used are indicated in the following tables:

4.1)

| Reactants | Quantities |
| --- | --- |
| NIPAM | 0.15 g |
| MBA | 0.0075 g |
| Potassium persulfate (KPS) | 0.0056 g |

The magnetic particles obtained have the references: ENC10, ENC11 and ENC13.

4.2)

| Reactants | Quantities |
| --- | --- |
| NIPAM | 0.15 g |
| MBA | 0.015 g |
| Potassium persulfate (KPS) | 0.0056 g |

The magnetic particles obtained have the references: ENC12 and ENC16.

These particles were characterized. The results are given in the following tables:

a) Diameter of the magnetic particles obtained

| Code | $D^{(a)}$ nm | $D_n^{(b)}$ nm | $D_w^{(b)}$ nm | $DI^{(c)}$ |
| --- | --- | --- | --- | --- |
| ENC10 | 500 | 380 | 388 | 1.02 |
| ENC11 | 810 | 385 | 388 | 1.006 |
| ENC13 | 1500 | 352 | 363 | 1.030 |
| ENC12 | 750 | 366 | 369 | 1.007 |
| ENC16 | 1000 | ND | ND | ND |

$(a)$ diameter measured by dynamic light scattering
$(b)$ diameter measured by transmission electron microscopy
$(c)$ polydispersity index
ND not determined.

b) Mass percentage of ferrite encapsulated in the polymer and the separation time

| Code | mass % of ferrite magnetization | mass % of ferrite complexometry | separation time min (*) |
| --- | --- | --- | --- |
| ENC10 | 35 | 43 | <20 |
| ENC11 | 23 | 40 | <20 |
| ENC13 | 38 | 36 | <20 |
| ENC12 | 16 | 23 | <30 |
| ENC16 | 40 | 45 | <5 |

(*) The separation time is determined using a GEN-PROBE magnet, Magnetic separation unit, catalog #1639, San Diego.

The colloids obtained are stable, monodisperse and have a separation time, under the action of a magnetic field, of less than 30 min, and more particularly less than 5 min (ENC16). The sizes obtained are reproducible from one synthesis to another and are between 0.1 and 10 µm, and the size distribution within the same preparation is very narrow (DI<1.03). The amount of ferrite encapsulated is between 40 and 45%. The encapsulation does not cause desorption of the magnetic particles since it has been checked that the difference between the adsorbed mass percentage and the mass percentage after encapsulation is very small.

What is claimed is:

1. Monodisperse superparamagnetic particles having a predetermined size of between 0.1 and 10 µm, comprising:
   a core based on a first polymer,
   an internal layer, called the magnetic layer, covering the core, based on a second polymer, wherein in said internal layer a magnetic material is distributed, and
   an external layer, called the encapsulation layer, optionally functionalized, covering the magnetic layer, based on a third polymer and having an ability to interact with at least one biological molecule to fix the at least one biological molecule to the particles, either directly or indirectly, wherein at least the second polymer is heat-sensitive and has a predetermined lower critical solubility temperature (LCST) of between 15 and 65° C.

2. The particles according to claim 1, wherein the second polymer is obtained by polymerization of (1) a water-soluble monomer of acrylamide or of an acrylamide derivative, (2) at least one crosslinking agent and (3) at least one functional, cationic and water-soluble monomer different from the monomer (1).

3. The particles according to claim 2, wherein the second polymer is poly(N-isopropylacrylamide) (PNIPAM) obtained by polymerization of (1) N-isopropylacrylamide, (2) N,N-methylenebisacrylamide and (3) 2-aminoethyl-methacrylate chloride.

4. The particles according to claim 2, wherein the first polymer is identical to the second polymer.

5. The particles according to claim 1, wherein the first polymer is different from the second polymer and is a polymer having a hydrophobic character.

6. The particles according to claim 1, wherein the third polymer is a hydrophilic polymer.

7. The particles according to claim 6, wherein the third polymer is functionalized and bears a functional group selected from the group consisting of carboxylic, aldehyde, thiol and amine functional groups.

8. The particles according to claim 1, said particles having an essentially spherical shape.

9. A process for obtaining particles as defined according to claim 1, comprising:
  (a) obtaining the first polymer by polymerization of the suitable monomer or monomers,
  (b) obtaining a sol of the second polymer by polymerization in aqueous phase of (1) a water-soluble monomer of acrylamide or of an acrylamide derivative, (2) at least one crosslinking agent and (3) at least one functional, cationic and water-soluble monomer different from the monomer (1),
  (c) bringing the magnetic material into contact with the first and second polymers at a temperature below the lower critical solubility temperature (LCST) of the second polymer to adsorb the magnetic material,
  (d) bringing the reaction mixture obtained in (c) to a temperature above the LCST of the second polymer to obtain the magnetic layer, and
  (e) bringing the mixture obtained in (d) into contact, in aqueous phase, with the monomer or monomers suitable for obtaining the third polymer by polymerization to encapsulate the mixture obtained in (d).

10. The process according to claim 9, wherein steps (a) and (b) are carried out simultaneously.

11. The process according to claim 10, wherein the first polymer is identical to the second polymer.

12. The process according to claim 9, wherein the first polymer is different from the second polymer and is a polymer having a hydrophobic character.

13. The process according to claim 9, wherein, for step (b) and optionally step (a), the monomer (1) is selected from the group consisting of N-alkylacrylamides and N,N-dialkylacrylamides.

14. The process according to claim 13, wherein the monomer (1) is selected from the group consisting of N-isopropylacrylamide, N-ethylmethacrylamide, N-n-propylacrylamide, N-n-propylmethacrylamide, N-isopropylmethacrylamide, N-cyclopropylacrylamide, N,N-diethylacrylamide, N-methyl-N-isopropylacrylamide, and N-methyl-N-n-propylacrylamide.

15. The process according to claim 9, wherein, for step (b) and optionally step (a), the functional monomer or monomers (3) are selected from the group consisting of acrylic and methacrylic derivatives, 2-aminoethyl-methacrylate (AEM) chloride, N-vinylpyridine derivatives, trialkylammonium derivatives and isothiouronium chloride derivatives.

16. The process according to claim 9, wherein, for step (b) and optionally step (a), the crosslinking agent (2) is water-soluble and is N,N-methylenebisacrylamide (MBA) or ethylene glycol dimethacrylate.

17. The process according to claim 9, wherein the third polymer is a hydrophilic polymer.

18. The particles according to claim 1, wherein the external layer has an ability to fix the at least one biological molecule to the particles, directly or indirectly, by adsorption or covalent bonding.

19. The particles according to claim 1, wherein said particles contain said magnetic material in an amount of from 25 to 80% by weight.

20. A process for isolating, in a liquid specimen, at least one biological molecule, comprising:
  bringing said specimen into contact with particles according to claim 1, by incubation, wherein said particles interact with said at least one biological molecule to fix the at least one biological molecule to the particles directly or indirectly via a ligand thereon;
  applying a magnetic field to the mixture obtained; and
  separating the particles from the specimen.

21. The process according to claim 20, wherein said at least one biological molecule is selected from the group consisting of proteins, antibodies, fragments of antibodies, antigens, polypeptides, enzymes, haptens, nucleic acids and fragments of nucleic acids.

22. The process according to claim 20, in which the at least one biological molecule is fixed to the particles, directly or indirectly, by adsorption or by covalent bonding.

23. A reactive medium for the isolation of biological molecules, the reactive medium comprising a dispersion, in aqueous medium, of particles as defined in claim 1.

* * * * *